US007683052B2

(12) United States Patent
Ali et al.

(10) Patent No.: US 7,683,052 B2
(45) Date of Patent: Mar. 23, 2010

(54) CRYSTALLINE POLYMORPH OF BAZEDOXIFENE ACETATE

(75) Inventors: Kadum A. Ali, Congers, NY (US);
Pietro Allegrini, San Donato Milanese (IT); Aldo Belli, Cornate d'Adda (IT); Roberto Brescello, Abano Terme (IT); Vincenzo Cannata, Borgonuovo di SassoMarconi (IT); Malama K. Chibwe, Royersford, PA (US); Livius Cotarca, Cervignano del Friuli (IT); Shridhar G. Gangolli, Park Ridge, NJ (US); Carl E. Longfellow, Warwick, NY (US); Giorgio Soriato, Caldiero (IT); Massimo Verzini, Caldiero (IT)

(73) Assignee: Wyeth, Madison, NJ (US)

( * ) Notice: Subject to any disclaimer, the term of this patent is extended or adjusted under 35 U.S.C. 154(b) by 704 days.

(21) Appl. No.: 11/100,998

(22) Filed: Apr. 6, 2005

(65) Prior Publication Data

US 2005/0250762 A1    Nov. 10, 2005

Related U.S. Application Data

(60) Provisional application No. 60/560,584, filed on Apr. 7, 2004.

(51) Int. Cl.
*A61P 5/30* (2006.01)
*A61K 31/55* (2006.01)
*C07D 403/02* (2006.01)

(52) U.S. Cl. .................... 514/217.08; 540/602
(58) Field of Classification Search ............ 514/217.08; 540/602
See application file for complete search history.

(56) References Cited

U.S. PATENT DOCUMENTS

| 5,780,497 | A | 7/1998 | Miller et al. |
| 5,880,137 | A | 3/1999 | Miller et al. |
| 5,998,402 | A | 12/1999 | Miller et al. |
| 6,242,605 | B1 | 6/2001 | Raveendranath et al. |
| 6,479,535 | B1 | 11/2002 | Pickar et al. |
| 2002/0031548 | A1 | 3/2002 | Benjamin et al. |
| 2004/0002535 | A1 | 1/2004 | Fensome et al. |
| 2005/0227965 | A1 | 10/2005 | Demerson et al. |

FOREIGN PATENT DOCUMENTS

| EP | 802183 | 10/1997 |
| EP | 802184 | 10/1997 |
| EP | 1336602 | 8/2003 |
| WO | WO 99/19293 | 4/1999 |
| WO | WO-99/19293 | 4/1999 |
| WO | WO 02/03987 | 1/2002 |
| WO | WO-2005/100316 | 10/2005 |

OTHER PUBLICATIONS

Miller, et al., "Design, Synthesis, and Preclinical Characterization of Novel, Highly Selective Indole Estrogens," *J. Med. Chem.* (2001) 44 (11):1654-1657 and supporting information.
Miller, et al., Drugs of the Future (2002) 27(2):117.
Greenberger, et al., "A New Antiestrogen, 2-(4-Hydroxy-phenyl)-3-methyl-1-[4-(2-piperidin-1-yl-ethoxy)-benzyl]-1H-indol-5-ol hydrochloride (ERA-923), Inhibits the Growth of Tamoxifen-sensitive and -resistant Tumors and Is Devoid of Uterotropic Effects in Mice and Rats," *Clinical Cancer Research* (2001) 7:3166-3177.
Biskobing, "Novel Therapies for Osteoporosis", Expert Opin Investig Drugs, 12(4):611-621 (2003)—Abstract Only.
Bryn, et al., "Chapter 10: Polymorphs", *Solid-State Chemistry of Drugs, Second Edition*, SSCI, Inc., West Lafayette, IN, pp. 143-231 (1999).
Miller, et al., "Bazedoxifene Acetate *Selective Estrogen Receptor Modulator Treatment and Prevention of Osteoporosis*", Drugs of the Future, 27(2): 117-121, 2002.
Proteau, "Steroid Hormones and Therapeutically Related Compounds", *Wilson and Gisvold's Textbook of Organic Medical and Pharmaceutical Chemistry*, Eleventh Edition, Chapter 23, pp. 767-817 (2004).
"CMU Seed Fund Project on Detection and Control of Pharmaceutical Polymorphism", Carnegie Mellon Department of Physics, http://andrew.cmu.edu/user/suter/polymorph.html, printed Apr. 3, 2008.
Doelker, "Caracteres Physicochimiques des Principes Actifs Leurs Consequences sur la Faisabilite et la Staiblite des Formes Galeniques", Pharma Pratiques, 9(5):399-409 (1999) (English Abstract).
Doelker, "Seance Thematique Modifications Cristallines et Transformations Polymorphes au Cors des Operations Galeniques", Ann Pharm Fr. 60:161-176 (2002)—English Language Abstract.
Jain, et al., "Polymorphism in Pharmacy", Indian Drugs, 23(6):315-329 (1986).
Miller, et al., "Design, Synthesis, and Preclinical Characterization of Novel, Highly Selective Indole Estrogens", J. Med. Chem., 44:1654-1657 (2001).
Otsuka, et al., "Effect of Polymorphic Forms of Bulk Powders on Pharmaceutical Properties of Carbamazepine Granules", Chem. Pharm. Bull., 47(6):852-856 (1999).
Singhal, et al., "Drug Polymorphism and Dosage Form Design: A Practical Perspective", Advanced Drug Delivery Reviews, 56:335-347 (2004).
Ulrich, "Crystallization", in Kirk-Othmer Encyclopedia of Chemical Technology, vol. 8, pp. 95-147, 2002.

*Primary Examiner*—Brenda L Coleman
(74) *Attorney, Agent, or Firm*—Wilmer Cutler Pickering Hale and Dorr LLP (57) ABSTRACT

The present invention is directed to a crystalline polymorph of bazedoxifene acetate, compositions containing the same, preparations thereof, and uses thereof.

41 Claims, 4 Drawing Sheets

CRYSTALLINE POLYMORPH OF BAZEDOXIFENE ACETATE

CROSS REFERENCE TO RELATED APPLICATIONS

This application claims the benefit of U.S. Ser. No. 60/560,584, filed Apr. 7, 2004, the disclosure of which is incorporated herein by reference in its entirety.

FIELD OF THE INVENTION

The present invention relates to a crystalline polymorph, designated form B, of the selective estrogen receptor modulator 1-[4-(2-azepan-1-yl-ethoxy)-benzyl]-2-(4-hydroxy-phenyl)-3-methyl-1H-indol-5-ol acetic acid (bazedoxifene acetate).

BACKGROUND OF THE INVENTION

Bazedoxifene acetate (1-[4-(2-azepan-1-yl-ethoxy)-benzyl]-2-(4-hydroxy-phenyl)-3-methyl-1H-indol-5-ol acetic acid), having the chemical formula shown below:

belongs to the class of drugs typically referred to as selective estrogen receptor modulators (SERMs). Consistent with its classification, bazedoxifene demonstrates affinity for estrogen receptors (ER) but shows tissue selective estrogenic effects. For example, bazedoxifene acetate demonstrates little or no stimulation of uterine response in preclinical models of uterine stimulation. Conversely, bazedoxifene acetate demonstrates an estrogen agonist-like effect in preventing bone loss and reducing cholesterol in an ovariectomized rat model of osteopenia. In an MCF-7 cell line (human breast cancer cell line), bazedoxifene acetate behaves as an estrogen antagonist. These data demonstrate that bazedoxifene acetate is estrogenic on bone and cardiovascular lipid parameters and antiestrogenic on uterine and mammary tissue and thus has the potential for treating a number of different disease or disease-like states wherein the estrogen receptor is involved.

U.S. Pat. Nos. 5,998,402 and 6,479,535 report the preparation of bazedoxifene acetate and characterize the salt as having a melting point of 174-178° C. The synthetic preparation of bazedoxifene acetate has also appeared in the general literature. See, for example, Miller et al., *J. Med. Chem.*, 2001, 44, 1654-1657, which reports the salt as a crystalline solid having a melting point of 170.5-172.5° C. Further description of the drug's biological activity has appeared in the general literature as well (e.g. Miller, et al. *Drugs of the Future,* 2002, 27(2), 117-121).

It is well known that the crystalline polymorph form of a particular drug is often an important determinant of the drug's ease of preparation, stability, solubility, storage stability, ease of formulation and in vivo pharmacology. Polymorphic forms occur where the same composition of matter crystallizes in a different lattice arrangement resulting in different thermodynamic properties and stabilities specific to the particular polymorph form. In cases where two or more polymorph substances can be produced, it is desirable to have a method to make both polymorphs in pure form. In deciding which polymorph is preferable, the numerous properties of the polymorphs must be compared and the preferred polymorph chosen based on the many physical property variables. It is entirely possible that one polymorph form can be preferable in some circumstances where certain aspects such as ease of preparation, stability, etc are deemed to be critical. In other situations, a different polymorph maybe preferred for greater solubility and/or superior pharmacokinetics.

Because improved drug formulations, showing, for example, better bioavailability or better stability are consistently sought, there is an ongoing need for new or purer polymorphic forms of existing drug molecules. The crystalline polymorph of bazedoxifene acetate described herein helps meet these and other needs.

SUMMARY OF THE INVENTION

The present invention provides a crystalline polymorph (form B) of bazedoxifene acetate characterized according to the powder X-ray diffraction data, IR data, and DSC data provided herein.

The present invention further provides compositions containing polymorphic form B of bazedoxifene acetate.

The present invention further provides a process for preparing crystalline polymorph B comprising combining bazedoxifene acetate with a solvent comprising ethanol to form a mixture, wherein the mixture is maintained at or above a temperature of about 25° C. for a time and under conditions suitable for forming polymorph form B.

The present invention further provides a process for increasing the proportion of bazedoxifene acetate form B in a composition comprising a mixture of form A and form B, wherein the process involves combining solvent comprising ethanol with the composition to form a mixture, wherein mixture is maintained at or above a temperature of about 25° C. for a time and under conditions suitable for increasing the proportion of Form B.

The present invention further provides a method of treating a mammal having a disease or syndrome associated with estrogen deficiency or excess of estrogen comprising administering to said mammal a therapeutically effective amount of form B polymorph of bazedoxifene acetate.

The present invention further provides a method of treating a mammal having a disease or disorder associated with proliferation or abnormal development of endometrial tissues comprising administering to said mammal a therapeutically effective amount of form B polymorph of bazedoxifene acetate.

The present invention further provides a method of lowering cholesterol in a mammal comprising administering to said mammal a therapeutically effective amount of form B polymorph of bazedoxifene acetate.

The present invention further provides a method of inhibiting bone loss or breast cancer in a mammal comprising administering to the mammal a therapeutically effective amount of form B polymorph of bazedoxifene acetate.

The present invention further provides a method of treating a postmenopausal woman for one or more vasomotor disturbances, such as hot flush, comprising administering to the postmenopausal woman a therapeutically effective amount of form B polymorph of bazedoxifene acetate.

The present invention further provides the crystalline polymorph form B of bazedoxifene acetate prepared by any of the methods described herein.

DETAILED DESCRIPTION

The present invention provides, inter alia, an anhydrous, non-solvated crystalline polymorph of bazedoxifene acetate, referred to herein as form B, which can be identified by one or more solid state analytical methods. For example, form B can be identified by its powder X-ray diffraction pattern which is provided in FIG. 1. Powder X-ray diffraction data consistent with form B is provided in Table 1 below.

TABLE 1

| Degree (2θ) | Intensity, Counts per Seconds (CPS) |
|---|---|
| 12.1 | 1530 |
| 13.3 | 3174 |
| 13.4 | 1758 |
| 14.5 | 1034 |
| 15.6 | 814 |
| 15.9 | 1249 |
| 16.9 | 710 |
| 18.8 | 700 |
| 19.4 | 1605 |
| 20.8 | 6982 |
| 21.6 | 2193 |
| 22.7 | 1225 |
| 22.8 | 1045 |
| 24.2 | 756 |
| 25.0 | 1809 |
| 26.0 | 705 |
| 29.9 | 833 |
| 30.5 | 994 |
| 34.2 | 1269 |

Figure 1:
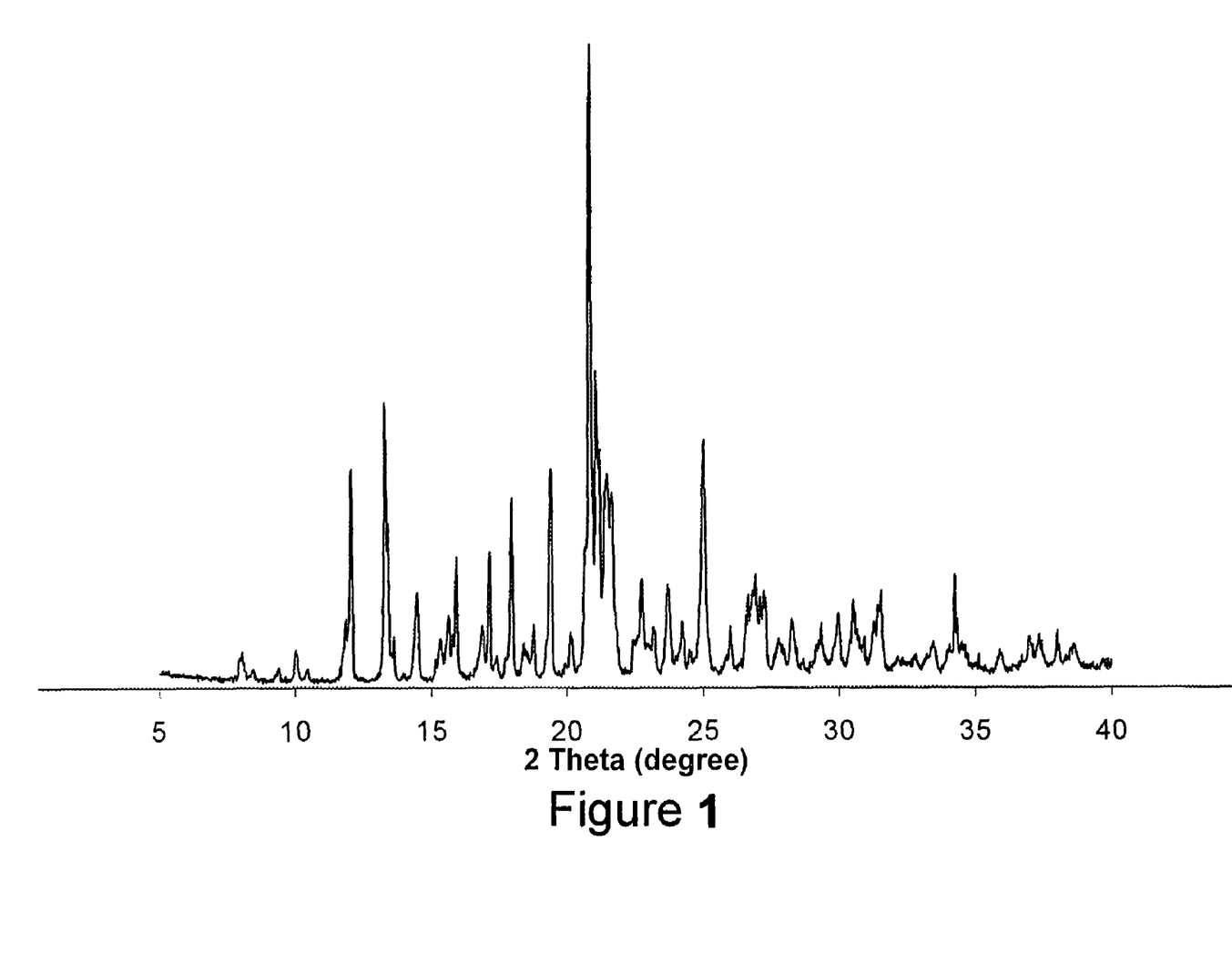
FIG. 1 depicts a powder X-ray diffraction pattern of the bazedoxifene acetate form B polymorph, where the diffraction angle ranges from 5° to 40° with a step of 0.02°.

In some embodiments, crystalline polymorph form B of bazedoxifene acetate is characterized as having a powder X-ray diffraction pattern having characteristic peaks, in terms of 2θ, at about 13.3° and about 20.8°. In some embodiments, the powder X-ray diffraction pattern further includes characteristic peaks, in terms of 2θ, at about 21.6° and about 25.0°. In some embodiments, form B is characterized by a powder X-ray diffraction pattern having 5 or more characteristic peaks, in terms of 2θ, selected from about 12.1°, about 13.3°, about 13.4°, about 14.5°, about 15.6°, about 15.9°, about 16.9°, about 18.8°, about 19.4°, about 20.8°, about 21.6°, about 22.7° about 22.8° about 24.2° about 25.0°, about 26.0°, about 29.9°, about 30.5°, and about 34.2°. In yet further embodiments, form B is characterized by a powder X-ray diffraction pattern substantially as shown in FIG. 1. The relative intensities of the peaks can vary, depending upon the sample preparation technique, the sample mounting procedure and the particular instrument employed. Moreover, instrument variation and other factors can affect the 2-theta values. Therefore, the XRPD peak assignments can vary by plus or minus about 0.2°.

Figure 2:
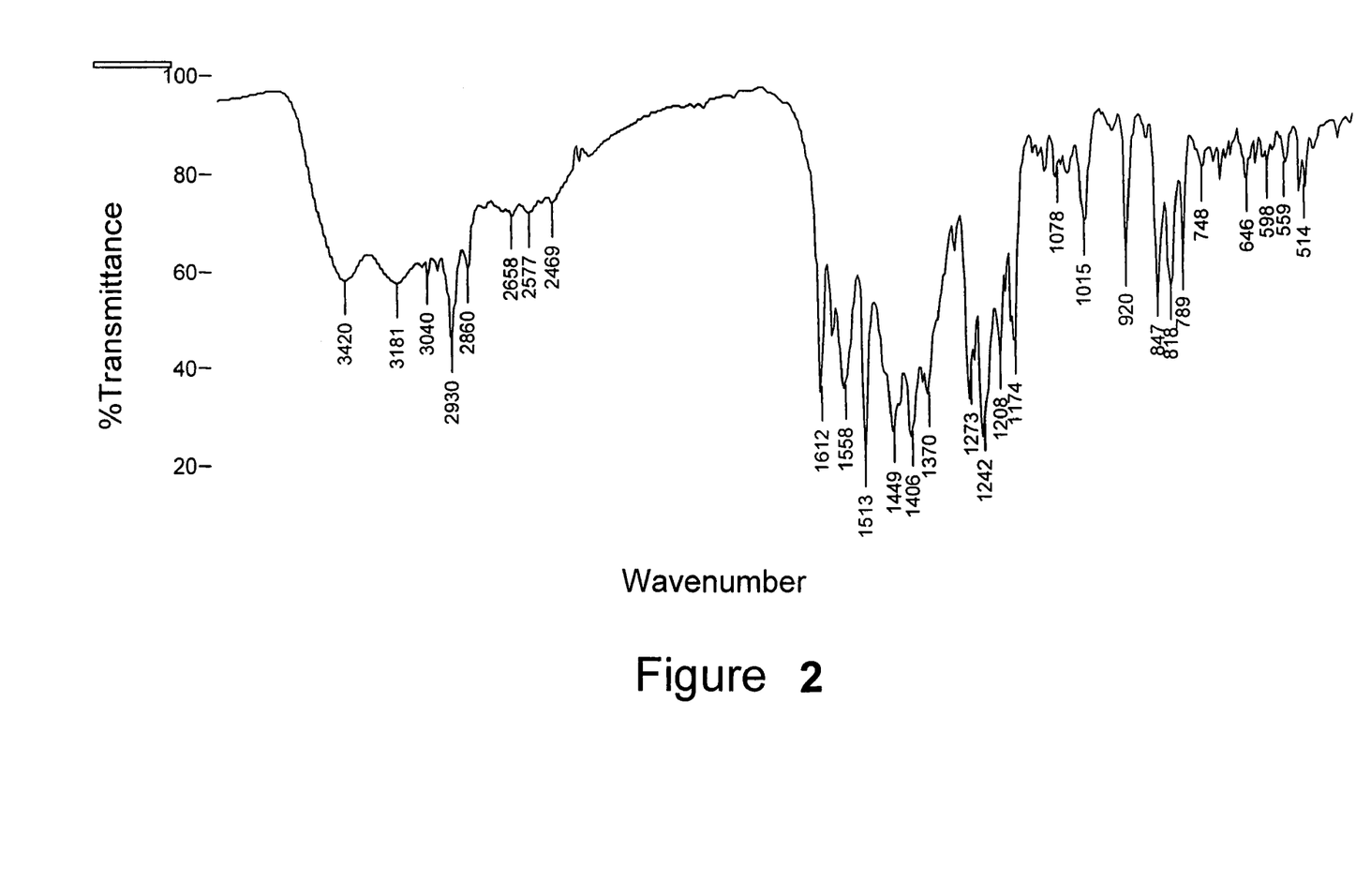
FIG. 2 depicts an IR spectrum of the bazedoxifene acetate form B polymorph in KBr pellet.

Form B can also be identified by IR spectroscopy such as provided in FIG. 2. For example, form B can be characterized by an infrared spectrum in KBr having one or more characteristic peaks selected from about 1513, about 1449, about 1406, and about 1242 cm$^{-1}$. In further embodiments, form B is characterized as having an infrared spectrum in KBr substantially as shown in FIG. 2.

Figure 3:
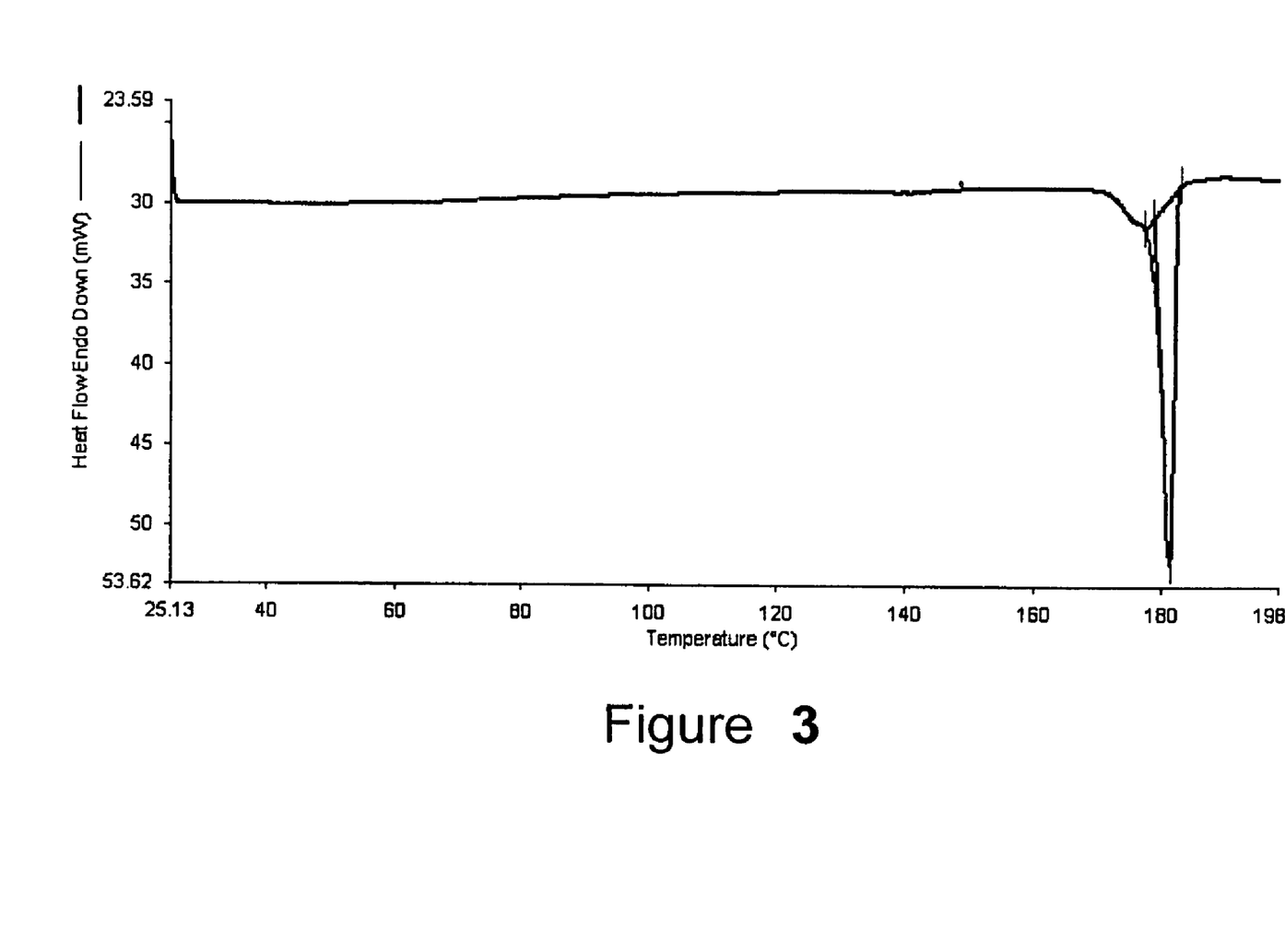
FIG. 3 depicts a differential scanning calorimetry (DSC) trace of bazedoxifene acetate form B polymorph.

Form B can also be identified by its characteristic differential calorimeter scanning (DSC) trace such as shown in FIG. 3. In some embodiments, form B is characterized by a DSC trace showing a maximum at about 181° C. For DSC, it is known that the temperatures observed will depend upon the rate of temperature change as well as sample preparation technique and the particular instrument employed. Thus, the values reported herein relating to DSC thermograms can vary by plus or minus about 4° C.

Baxedoxifene acetate polymorphic form B is readily distinguishable from other crystalline polymorphs, such as the less thermodynamically stable form A. Sample data for several physical properties are compared for form A and form B polymorphs below in Table 2.

TABLE 2

| Measurement | Form A | Form B |
|---|---|---|
| Melting Point | 176° C. | 181° C. |
| Heat of Fusion | 94.6 J/G | 108.4 J/G |
| Solubility-Water | 0.49 mg/mL | 0.23 mg/mL |
| Solubility-Org (EtOH/EtAc/Tol) | 24.5 mg/mL | 12.4 mg/mL |
| Intrinsic Dissolution Rate | 0.125 mg/cm$^2$-min | 0.09 mg/cm$^2$-min |
| DSC | Single Melting Endotherm 176.1° C. | Single Melting Endotherm 181.1° C. |
| TGA | Similar | Similar |
| X-Ray Powder | 12.7°, 16.0°, 18.5°, 20.7°, 22.3° (2θ) | 13.3°, 20.8°, 21.6°, 25.0° (2θ) |
| Raman/IR | 1511, 1467 cm$^{-1}$ | 1513, 1449, 1406 cm$^{-1}$ |

As can be seen in Table 2, the two crystalline polymorphs have discernable physical and spectroscopic characteristics. Form B appears to be thermodynamically more stable than form A, contributing to numerous advantages. For example, the increased stability of form B would facilitate manufacturing and purification processes. Form B would also be expected to have better resistance to degradation brought on by, for example, exposure to high temperatures and/or humidity, and have a longer shelf-life than form A or amorphous material.

Bazedoxifene acetate form B can be prepared by, for example, combining bazedoxifene acetate (e.g., form A polymorph or amorphous material) with a solvent containing an alcohol and maintaining the resulting mixture at or above a temperature of about 25° C. (e.g., about 25 to about 35° C. or about 30° C.) for a time sufficient to produce form B (e.g., more than about 1 hour, more than about 2 hours, about 1 to about 48 hours, about 1 to about 24 hours, or about 1 to about 12 hours). The mixture can optionally be cooled to a temperature below about 25° C. (e.g., about −5 to about 25° C., about −5 to about 15, about −5 to about 10, or about 0° C., to induce further precipitation. Form B seed crystals, obtained from a previous preparation, can be optionally added during the cooling process. Solvent can be provided in an amount sufficient to dissolve substantially all or less than all of the bazedoxifene acetate starting material forming homogenous or heterogenous mixtures, respectively. Weight ratio of total solvent to amount of bazedoxifene actetate can be, for example, about 5:1, about 3:1, about 2:1, or about 1:1.

Bazedoxifene acetate containing form A can be prepared by, for example deprotecting hexamethylene benzyloxyindole (preparation provided in, e.g., U.S. Pat. No. 5,998,402) by hydrogenolysis in a solvent containing an alcohol in the presence of a hydrogenation catalyst (e.g., 10% palladium on charcoal; Pd/C 10%). Hydrogenolysis can be carried out for any length of time and is typically carried out until the reaction is substantially complete as can be monitored by HPLC or any other suitable technique. The catalyst can be subsequently removed by filtration and an antioxidant (e.g., ascorbic acid) added to inhibit possible oxidative degradation of the hydrogenated product. Example suitable weight ratios of solvent to hexamethylene benzyloxyindole include, for example, about 10:1 to about 2:1, about 8:1 to about 4:1, or about 6:1 to about 7:1.

Acetic acid can be added to the hydrogenated product (bazedoxifene free base), forming the acetate salt. Suitable amounts of acetic acid are typically sufficient to convert all free base present in the reaction mixture to salt form. Accordingly, one or more equivalents of acetic acid (relative to amount of hexamethylene benzyloxyindole starting material) can be added. In some embodiments, about 1 to about 2 equivalents of acetic acid are added. The full desired amount of acetic acid can be added in one or multiple portions. Crystalline product typically precipitates out of solution upon addition of the acetic acid and can be recrystallized from an alcohol-containing solvent according to routine methods.

The steps involved in the preparation of form A can be carried out at any suitable temperature, such as at or below about 25° C. For example, hydrogenation can be carried out at ambient temperature such as 25° C. Addition of acetic acid can be carried out at about 20° C. or lower. Reaction mixture containing bazedoxifene acetate can be maintained for any length of time (e.g., at least about 1 hr, at least about 2 hrs, at least about 6 hr, or at least about 12 hrs) at a temperature from about −20 to about 20° C. In some embodiments, the reaction mixture is held for at least about 2 hours at 20° C. In some embodiments, the reaction mixture is held for at least about 2 hours at 0° C.

The present invention is further directed to a process for increasing the proportion of form B in a composition containing a mixture of form A and form B. In some embodiments, form B comprises less than about 10%, less than about 20%, less than about 30%, or less than about 40% by weight of total bazedoxifene acetate in the starting composition. Proportion of form B can be increased by combining solvent containing an alcohol with the starting composition and maintaining the resulting mixture at or above a temperature of about 25° C. (e.g., about 25 to about 60, about 25 to about 40, or about 25 to about 30° C.) for a length of time suitable for increasing the proportion of form B in the composition. Solvent can be provided in an amount sufficient to dissolve substantially all or less than all of the bazedoxifene acetate starting material forming homogenous or heterogenous mixtures, respectively. The solvent can be provided in a weight ratio of total solvent to amount of bazedoxifene starting material of, for example, about 5:1, about 3:1 about 2:1, or about 1:1.

Suitable alcohols in connection with any of the processes above include methanol, ethanol, denatured ethanol (e.g., denatured with about 1-10% toluene, 1-10% hexane, 1-10% ethyl acetate), isopropanol, mixtures thereof and the like. In some embodiments, the alcohol is ethanol which can be optionally denatured with about 1-10% v/v toluene, about 1-10% v/v hexanes, about 1-10% v/v ethyl acetate, and the like. In further embodiments, the reaction solvent and/or recrystallizing solvent for any of the above processes is ethanol containing 5% (by volume) ethyl acetate. In yet further embodiments, the solvent can be a mixture of ethanol and ethyl acetate in a v/v ratio of about 50:1, about 20:1, about 10:1. about 6:1, about 4:1, or about 3:1. In further embodiments, the solvent is ethanol.

In some embodiments, the mixture of bazedoxifene acetate and solvent is heated to reflux temperature, such as for several hours (e.g., about 1 to about 3 hours) then slowly cooled in a stepwise fashion. For example, the mixture can be cooled to about 45 to about 55° C. (e.g., about 50° C.) over the course of a first time period and then cooled to about 10 to about 30° C. (e.g., about 20° C.) over the course of a second time period. First, second, and any additional time periods can last for several hours such as from about 1 to about 5 hours or about 1 to about 3 hours. In some embodiments, the first time period is about 1 hour and the second time period is about 3 hours. The mixture can further be maintained at the cooled temperature (e.g, about 10 to about 30° C.) for an additional time period sufficient for precipitation of product. The additional time period can be, for example, 2 hours to about 24 hours, about 8 to about 18 hours, or about 13 hours.

The methods for preparation of form B provided herein can result in substantially pure form B (e.g., compositions containing less than about 10%, about 5%, or about 3% of form A) as well as mixtures enriched in form B (e.g., greater than about 50% form B relative to form A). Accordingly, the present invention further provides compositions containing form B. In some embodiments, at least about 50%, at least about 70%, at least about 80%, at least about 90%, at least about 95%, at least about 97%, at least about 98%, or at least about 99% by weight of total bazedoxifene acetate in a composition is present as form B. In further embodiments, compositions of the present invention consist essentially of bazedoxifene acetate where at least about 95%, at least about 97%, at least about 98%, or at least about 99% of the bazedoxifene acetate is present in the composition as form B. Respective amounts of polymorphic forms of bazedoxifene acetate in a composition can be determined by any suitable spectroscopic method, such as X-ray powder diffraction.

Methods

As described in U.S. Pat. No. 5,998,402, bazedoxifene and salts thereof are selective estrogen agonists with affinity for the estrogen receptor. Unlike other types of estrogen agonists, bazedoxifene and salts thereof are antiestrogenic in the uterus and can antagonize the trophic effects of estrogen agonists in uterine tissues. Accordingly, polymorphs of bazedoxifene acetate and compositions containing the same can find many uses related to treating disease states or syndromes associated with an estrogen deficiency or an excess of estrogen. The polymorph can also be used in methods of treatment for diseases or disorders which result from proliferation or abnormal development, actions or growth of endometrial or endometrial-like tissues.

The present polymorphic form of bazedoxifene acetate has the ability to behave like an estrogen agonist by lowering cholesterol and inhibiting bone loss. Accordingly, the polymorph is useful for treating many maladies which result from estrogen effects and estrogen excess or deficiency including osteoporosis, prostatic hypertrophy, male pattern baldness, vaginal and skin atrophy, acne, dysfunctional uterine bleeding, endometrial polyps, benign breast disease, uterine leiomyomas, adenomyosis, ovarian cancer, infertility, breast cancer, endometriosis, endometrial cancer, polycystic ovary syndrome, cardiovascular disease, contraception, Alzheimer's disease, cognitive decline and other CNS disorders, as well as certain cancers including melanoma, prostrate cancer, cancers of the colon, CNS cancers, among others. Additionally, these polymoprhs can be used for contraception in pre-menopausal women, as well as hormone replacement therapy in post-menopausal women (such as for treating vasomotor disturbances such as hot flush) or in other estrogen deficiency states where estrogen supplementation would be beneficial. It can also be used in disease states where amenorrhea is advantageous, such as leukemia, endometrial ablations, chronic renal or hepatic disease or coagulation diseases or disorders.

The polymorph of the invention can also be used in methods of inhibiting bone loss. Bone loss often results from an imbalance in an individual's formation of new bone tissues and the resorption of older tissues, leading to a net loss of bone. Such bone depletion results in a range of individuals, particularly in post-menopausal women, women who have undergone bilateral oophorectomy, those receiving or who have received extended corticosteroid therapies, those experiencing gonadal dysgenesis, and those suffering from Cushing's syndrome. Special needs for bone, including teeth and oral bone, replacement can also be addressed using these polymorphs in individuals with bone fractures, defective bone structures, and those receiving bone-related surgeries and/or the implantation of prosthesis. In addition to the problems described above, the polymorph can be used in treatments for osteoarthritis, hypocalcemia, hypercalcemia, Paget's disease, osteomalacia, osteohalisteresis, multiple myeloma and other forms of cancer having deleterious effects on bone tissues.

Methods of treating the diseases and syndromes listed herein are understood to involve administering to an individual in need of such treatment a therapeutically effective amount of the polymorph of the invention, or composition containing the same. As used herein, the term "treating" in reference to a disease is meant to refer to preventing, inhibiting and/or ameliorating the disease.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) preventing the disease; for example, preventing a disease, condition or disorder in an individual that may be predisposed to the disease, condition or disorder but does not yet experience or display the pathology or symptomatology of the disease;

(2) inhibiting the disease; for example, inhibiting a disease, condition or disorder in an individual that is experiencing or displaying the pathology or symptomatology of the disease, condition or disorder (i.e., arresting or slowing further development of the pathology and/or symptomatology); and (3) ameliorating the disease; for example, ameliorating a disease, condition or disorder in an individual that is experiencing or displaying the pathology or symptomatology of the disease, condition or disorder (i.e., reversing the pathology and/or symptomatology).

Dosage and Formulation

The invention also includes pharmaceutical compositions utilizing one or more of the present polymorphs along with one or more pharmaceutically acceptable carriers, excipients, etc.

Formulations of bazedoxifene acetate form B include therapeutically effective amounts that can be given in daily doses ranging from 0.1 mg to 1000 mg to a person in need. Example dose ranges vary from 10 mg/day to about 600 mg/day or from 10 mg/day to about 60 mg/day. The dosing can be either in a single dose or two or more divided doses per day. Such doses can be administered in any manner that facilitates the compound's entry into the bloodstream including orally, via implants, parenterally (including intravenous, intraperitoneal, and subcutaneous injection), vaginally, rectally, and transdermally.

In some embodiments, the formulations can be administered transdermally which includes all administrations across the surface of the body and the inner linings of body passages including epithelial and mucosal tissues. Such administration can be in the form of a lotion, cream, colloid, foam, patch, suspension, or solution.

Oral formulations containing form B can comprise any conventionally used oral forms, including tablets, capsules, buccal forms, troches, lozenges and oral liquids suspensions or solutions. Capsules may contain mixtures of the crystalline form B in the desired percentage together any other polymorph(s) of bazedoxifene acetate or amorphous bazedoxifene acetate. Capsules or tablets of the desired crystalline form of the desired percentage composition may also be combined with mixtures of other active compounds or inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Tablet formulations can be made by conventional compression, wet granulation, or dry granulation methods and utilize pharmaceutically acceptable diluents (fillers), binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations used herein can utilize standard delay or time release formulations or spansules. Suppository formulations can be made from traditional materials, including cocoa butter, with or without the addition of waxes to alter the suppositories melting point, and glycerin. Water soluble suppository bases, such as polyethylene glycols of various molecular weights, can also be used.

Example excipient systems suitable for preparing formulations of the present polymorph include one or more fillers, disintegrants, and lubricants.

The filler component can be any filler component known in the art including, but not limited to, lactose, microcrystalline cellulose, sucrose, mannitol, calcium phosphate, calcium carbonate, powdered cellulose, maltodextrin, sorbitol, starch, or xylitol.

Disintegrants suitable for use in the present formulations can be selected from those known in the art, including pregelatinized starch and sodium starch glycolate. Other useful disintegrants include croscarmellose sodium, crospovidone, starch, alginic acid, sodium alginate, clays (e.g. veegum or xanthan gum), cellulose floc, ion exchange resins, or effervescent systems, such as those utilizing food acids (such as citric acid, tartaric acid, malic acid, fumaric acid, lactic acid, adipic acid, ascorbic acid, aspartic acid erythorbic acid, glutamic acid, and succinic acid) and an alkaline carbonate component (such as sodium bicarbonate, calcium carbonate, magnesium carbonate, potassium carbonate, ammonium carbonate, etc.). The disintegrant(s) useful herein can comprise from about 4% to about 40% of the composition by weight, preferably from about 15% to about 35%, more preferably from about 20% to about 35%.

The pharmaceutical formulations can also contain an antioxidant or a mixture of antioxidants, such as ascorbic acid. Other antioxidants which can be used include sodium ascorbate and ascorbyl palmitate, preferably in conjunction with an amount of ascorbic acid. An example range for the antioxidant(s) is from about 0.5% to about 15% by weight, most preferably from about 0.5% to about 5% by weight.

An example oral formulation contains the present polymorph and the following excipient systems:
  a) a filler and disintegrant together comprising from about 5% to about 82% by weight (wght) of the total formulation, preferably between about 30% and about 80% of the formulation, wherein from about 4% to about 40% by weight of the total formulation comprises one or more pharmaceutically acceptable disintegrants; and
  b) a lubricant comprising from about 0.2% to about 10% of the composition (wght), such as selected from the group of magnesium stearate or other metallic stearates (e.g. calcium stearate or zinc stearate), fatty acid esters (e.g. sodium stearyl fumarate), fatty acids (e.g. stearic acid), fatty alcohols, glyceryl behenate, mineral oil, parrafins. hydrogenated vegetable oils, leucine, polyethylene glycols, metallic lauryl sulfates and sodium chloride.

A further excipient system can comprise:
  a) filler and distintegrant together comprising from about 5.4% to about 89%, by weight or preferably from about 32.5% to about 87% by weight; and
  b) lubricant comprising from about 0.22% to about 10.9% by weight.

The excipient systems can also optionally utilize pharmaceutically acceptable wetting agents, glidants and antioxidants. Such systems can comprise:
  a) a filler and disintegrant component together comprising from about 5% to about 82% by weight (wght) of the total formulation, preferably between about 30% and about 80% of the formulation, wherein from about 4% to about 40% by weight of the total formulation comprises one or more pharmaceutically acceptable disintegrants;
  b) optionally, a wetting agent comprising from about 0.2 to about 5% of the composition (wght), such as selected from the group of sodium lauryl sulfate, polyoxyethylene sorbitan fatty acid esters, polyoxyethylene alkyl ethers, sorbitan fatty acid esters, polyethylene glycols, polyoxyethylene castor oil derivatives, docusate sodium, quaternary ammonium compounds, sugar esters of fatty acids and glycerides of fatty acids;
  c) a lubricant comprising from about 0.2% to about 10% of the composition (wght), such as selected from the group of magnesium stearate or other metallic stearates (e.g. calcium stearate or zinc stearate), fatty acid esters (e.g. sodium stearyl fumarate), fatty acids (e.g. stearic acid), fatty alcohols, glyceryl behenate, mineral oil, parrafins, hydrogenated vegetable oils, leucine, polyethylene glycols, metallic lauryl sulfates and sodium chloride; and
  d) optionally, a glidant comprising from about 0.1% to about 10% (wght) of the final composition, the glidant selected from those known in the art, including from the group of silicon dioxide, talc, metallic stearates, calcium silicate, or metallic lauryl sulfates.

Further excipient systems, according to the present invention, can include, by weight:
  a) a filler and disintegrant together comprising between about 54% and about 80% of the formulation, with the disintegrant agent(s) therein comprising from about 4% to about 40% by weight of the overall formulation;
  b) a wetting agent comprising between about 0.55% and about 2.5% of the formulation;
  c) a lubricant comprising between about 0.2% and about 5.5% of the formulation; and
  d) a glidant comprising between about 0.1% and about 5.0% of the formulation.

The excipient systems above also optionally contain an antioxidant component, e.g., ascorbic acid, at a concentration of from about 0.5% to about 5.0% by weight.

Among further excipient systems of this invention are those comprising:
  a) a filler and disintegrant, as described above, together comprising between about 50% and about 87% of the formulation, where the disintegrant(s) therein comprises from about 25% to about 35% of the formulation, by weight;
  b) a wetting agent comprising between about 0.55% and about 2.7% of the formulation;
  c) a lubricant comprising between about 0.2% and about 5.5% of the formulation;
  d) a glidant comprising between about 0.1% and about 5.5% of the formulation; and
  e) an antioxidant component, such as ascorbic acid, in an amount of from about 0.5% to about 5.5% by weight.

The percentages listed above for the filler, disintegrant, lubricant and other components are based on final pharmaceutical composition. The remaining percentage of the final composition is comprised of the active pharmacological agent(s) and optionally a pharmaceutically acceptable surface covering, such as a coating or capsule, as described herein. In some embodiments of this invention, the active pharmacological agent(s) comprise from about 0.5% to about 20%, by weight, of the final composition, more preferably from about 1% to about 5%, and the coating or capsule comprises up to about 8%, by weight, of the final composition.

The formulations described herein can be used in an uncoated or non-encapsulated solid form. In some embodiments, the pharmacological compositions are optionally coated with a film coating, for example, comprising from about 0.3% to about 8% by weight of the overall composition. Film coatings useful with the present formulations are known in the art and generally consist of a polymer (usually a cellulosic type of polymer), a colorant and a plasticizer. Additional ingredients such as wetting agents, sugars, flavors, oils and lubricants may be included in film coating formulations to impart certain characteristics to the film coat. The compositions and formulations herein may also be combined and processed as a solid, then placed in a capsule form, such as a gelatin capsule.

Pharmaceutical compositions of bazedoxifene acetate can be formulated with steroidal estrogens, such as conjugated estrogens, USP. The amount of bazedoxifene acetate used in the formulation can be adjusted according to the particular polymorph form or ratio of polymorph forms used, the amount and type of steroidal estrogen in the formulation as well as the particular therapeutic indication being considered. In general, the bazedoxifene acetate of defined polymorphic composition ratio can be used in an amount sufficient to antagonize the effect of the particular estrogen to the level desired. The dose range of conjugated estrogens can be from about 0.3 mg to about 2.5 mg, about 0.3 mg to about 1.25 mg, or about 0.3 mg to about 0.625 mg. An example range for amount of bazedoxifene acetate in a combination formulation is about 10 mg to about 40 mg. For the steroidal estrogen mestranol, a daily dosage can be from about 1 µG to about 150 µG, and for ethynyl estradiol a daily dosage of from about 1 µG to 300 µG can be used. In some embodiments, the daily dose is between about 2 µG and about 150 µG.

In order that the invention disclosed herein may be more efficiently understood examples are provided below. It should be understood that these examples are for illustrative purposes only and are not to be construed as limiting the invention in any manner.

EXAMPLES

Example 1

Preparation of Bazedoxifene Acetate Form A Polymorph

A 2 gal hydrogenation vessel with agitator was charged with hexamethyleneimino benzyloxyindole (250 g, 0.3841 mols; see U.S. Pat. No. 5,998,402 for a preparation); ethanol (denatured with 5% by volume ethyl acetate) (1578 g, 2000 mL), and palladium on carbon 10% (25 g). The reactants were hydrogenated at 25° C. and 50 psi for 20 hours. Reaction progress was monitored by HPLC (Column: CSC-S ODS 2, 25 cm; Mobile phase: 20% 0.02 M $NH_4H_2PO_4$ (2 mL TEA/L, pH=3) and 80% MeCN; Flow: 2 mL/min; Detector: 220 nm). The reaction was considered complete when less than 1% of either the hexamethyleneimino benzyloxyindole (18.2 min retention time) or mono-debenzylated derivative thereof (5.1 min retention time) was detected.

The mixture was filtered through a cartridge which was subsequently rinsed with ethanol (denatured with 5% by volume ethyl acetate) (2×198 g, 2×250 mL). The filtrate was transferred to a 5 L multi-neck flask with agitator charged with L-ascorbic acid (2.04 g, 0.0116 mols) under nitrogen. Acetic acid (34.6 g, 0.5762 moles) was added at 20° C. while stirring. The resulting reaction mixture was stirred for 2 hours (pH was about 5 and crystallization began within about 10 minutes of addition of acetic acid). The reaction mixture was then cooled to 0° C. and maintained at this temperature for 2 hours. The resulting solid was collected by filtration on a Buchner funnel and washed with ethanol (denatured with 5% by volume ethyl acetate) (2×150 g, 2×190 mL) at 0° C.

The solid product was further purified by charging a 3 L multineck flask (with agitator, thermometer, and condenser under nitrogen) with the filtered solid, ethanol (denatured with 5% by volume ethyl acetate) (1105 g, 1400 mL), and L-ascorbic acid (1.73 g, 0.01 mols). The resulting mixture was heated to 75° C. and cooled to 20° C. over the course of 2 hours. The resulting suspension was further cooled to 0° C. and held at this temperature for 2 hours. The resulting solid product was collected by filtration with a Buchner funnel and washed with ethanol (denatured with 5% by volume ethyl acetate) (2×79 g, 2×100 mL) at 0° C. The product was dried in vacuo at 60° C., 5 mm Hg for 24 hours giving 151.3 g bazedoxifene acetate form A (74.2% yield).

Example 2

Preparation of Bazedoxifene Acetate Form B from Form A

To a stirred solution of 594 g of ethanol (denatured with 5% of acetone and with 3% of cyclohexane) and 184 g of ethyl acetate, 400 g of pure bazedoxifene acetate form A were added under nitrogen (e.g., see Example 1). The heterogeneous mixture was kept at 30° C. and stirred overnight under nitrogen.

The completion of the crystalline transformation was determined by DSC analysis. The mixture was cooled to 0° C. and stirred for 2 hrs under nitrogen. The product was filtered, washed with a mixture of denatured ethanol and ethyl acetate as above and dried overnight at 60° C. under vacuum giving 391 g (97.7% yield) of bazedoxifene acetate form B polymorph.

A substantially identical result was obtained using absolute ethanol or ethanol denatured with 5% toluene.

Example 3

Preparation of Bazedoxifene Acetate Form B from a Mixture of Form A and Form B

Bazedoxifene acetate form A (298 g) and bazedoxifene acetate form B (2 g) were suspended in a degassed mixture of ethyl acetate (400 mL) and ethyl alcohol (2400 mL). The resulting mixture was heated at reflux temperature for 2 hours. The suspension was cooled to 50° C. over the course of 1 hour and then to 20° C. over the course of 3 hours. The mixture was maintained at 20° C. for 13 hours and the product was recovered by filtration and washing with ethyl alcohol (78.9 g divided in 2 portions). The wet material was dried under vacuum at 60° C. resulting in 276.8 g of bazedoxifene acetate form B.

Example 4

X-Ray Powder Diffraction (XRPD)

XRPD analyses (see, e.g., FIG. 1) were carried out on a (Scintag X2) X-ray powder diffractometer using Cu K α radiation. The instrument was equipped with tube power, and amperage was set at 45 kV and 40 mA. The divergence and scattering slits were set at 1° and the receiving slit was set at 0.2 mm. A theta-two theta continuous scan at 3°/min (0.4 sec/0.02° step) from 3 to 40 °2θ was used.

Example 5

Infrared (IR) Spectroscopy

IR spectra (see, e.g., FIG. 2) were acquired as follows. Samples were prepared as potassium bromide (KBr) discs (or pellets). A small amount of each sample (about 3 mg) was ground in a hard surface mortar until glossy in appearance. One half gram (0.5 g) of KBr was added to the sample and the mixture was continuously ground until well mixed. The mixture was then transferred to a die and pressed into a disc using a hydraulic press.

The IR spectrum was obtained using a DIGILAB EXCALIBUR Series FTS-4000 FT-IR Spectrometer operated at 4 $cm^{-1}$ resolution and 16 scans between 400-4000 $cm^{-1}$.

Example 6

Differential Scanning Calorimetry (DSC)

Figure 4:
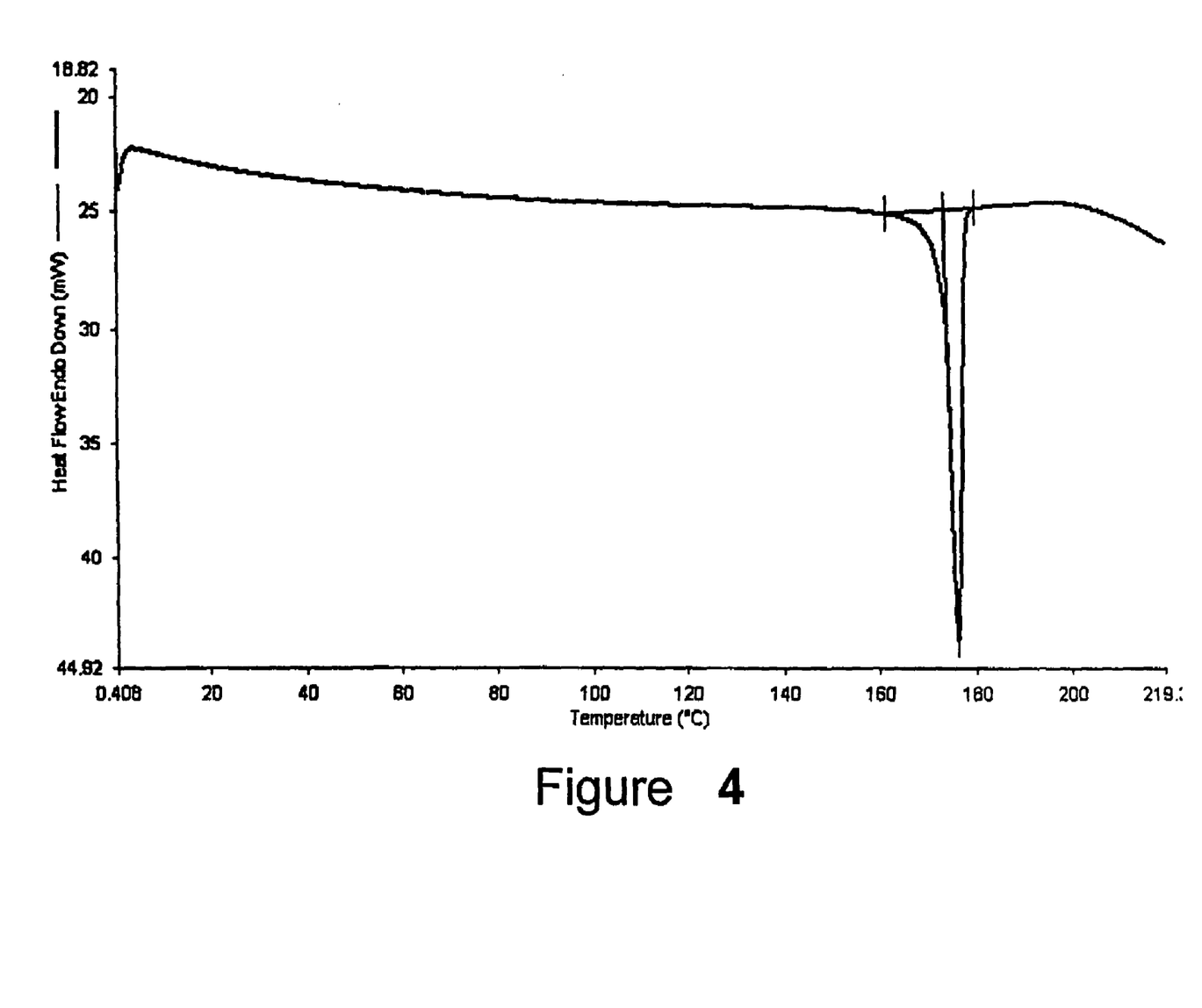
FIG. 4 depicts a differential scanning calorimetry (DSC) trace of bazedoxifene acetate form A polymorph as a comparison.

DSC measurements (see, e.g., FIGS. 3 and 4) were carried out in both sealed pan and vented pan at a scan rate of 10° C./min from 25° C. to 200° C. under nitrogen purge using a Pyris I DSC from Perkin-Elmer.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

What is claimed is:

1. A crystalline polymorph (form B) of bazedoxifene acetate having a powder X-ray diffraction pattern comprising characteristic peaks, in terms of 2θ, at about 13.3° and about 20.8°.

2. The polymorph of claim 1 wherein said powder X-ray diffraction pattern further comprises characteristic peaks, in terms of 2θ, at about 21.6° and about 25.0°.

3. The polymorph of claim 1 wherein said powder X-ray diffraction pattern comprises at least 5 characteristic peaks, in terms of 2θ, selected from about 12.1°, about 13.3°, about 13.4°, about 14.5°, about 15.6°, about 15.9°, about 16.9°, about 18.8°, about 19.4°, about 20.8°, about 21.6°, about 22.7°, about 22.8°, about 24.2°, about 25.0°, about 26.0°, about 29.9°, about 30.5°, and about 34.2°.

4. The polymorph of claim 1 having a powder X-ray diffraction pattern substantially as shown in FIG. 1.

5. The polymorph of claim 1 having an infrared spectrum in KBr comprising one or more characteristic peaks selected from about 1513, about 1449, about 1406, and about 1242 $cm^{-1}$.

6. The polymorph of claim 1 having an infrared spectrum in KBr substantially as shown in FIG. 2.

7. The polymorph of claim 1 having a differential scanning calorimetry trace showing a maximum at about 181° C.

8. The polymorph of claim 1 having a differential scanning calorimetry trace substantially as shown in FIG. 3.

9. A solid composition comprising the polymorph of claim 1.

10. The composition of claim 9 wherein at least about 50% by weight of total bazedoxifene acetate in said composition is present as said polymorph.

11. The composition of claim 9 wherein at least about 70% by weight of total bazedoxifene acetate in said composition is present as said polymorph.

12. The composition of claim 9 wherein at least about 80% by weight of total bazedoxifene acetate in said composition is present as said polymorph.

13. The composition of claim 9 wherein at least about 90% by weight of total bazedoxifene acetate in said composition is present as said polymorph.

14. The composition of claim 9 wherein at least about 95% by weight of total bazedoxifene acetate in said composition is present as said polymorph.

15. The composition of claim 9 wherein at least about 97% by weight of total bazedoxifene acetate in said composition is present as said polymorph.

16. The composition of claim 9 wherein at least about 98% by weight of total bazedoxifene acetate in said composition is present as said polymorph.

17. The composition of claim 9 wherein at least about 99% by weight of total bazedoxifene acetate in said composition is present as said polymorph.

18. A solid composition comprising the polymorph of claim 1 and, a pharmaceutically acceptable carrier.

19. A solid composition consisting essentially of bazedoxifene acetate wherein at least 95% by weight of said bazedoxifene acetate is present in said composition as the polymorph of claim 1.

20. A solid composition consisting essentially of bazedoxifene acetate wherein at least 97% by weight of said bazedoxifene acetate is present in said composition as the polymorph of claim 1.

21. A solid composition consisting essentially of bazedoxifene acetate wherein at least 98% by weight of said bazedoxifene acetate is present in said composition as the polymorph of claim 1.

22. A solid composition consisting essentially of bazedoxifene acetate wherein at least 99% by weight of said bazedoxifene acetate is present in said composition as the polymorph of claim 1.

23. A solid composition comprising the polymorph of any one of claims 1 to 8 and one or more steroidal estrogens selected from the group consisting of mestranol and ethynyl estradiol.

24. A process for preparing the polymorph of claim 1 comprising combining bazedoxifene acetate with a solvent comprising ethanol to form a mixture, wherein said mixture is maintained at or above a temperature of about 25° C. for a time and under conditions suitable for forming said polymorph.

25. The process of claim 24 wherein said mixture is a heterogeneous mixture.

26. The process of claim 24 wherein said mixture is maintained at or above a temperature of about 25° C. for more than about 2 hours.

27. The process of claim 24 wherein said mixture is maintained at a temperature of about 25 to about 35° C.

28. The process of claim 24 further comprising cooling said mixture to a temperature of below about 25° C.

29. The process of claim 24 wherein said solvent further comprises ethyl acetate.

30. A process for increasing the proportion of bazedoxifene acetate form B in a composition comprising a mixture of form A and form B, said process comprising combining solvent comprising ethanol with said composition to form a mixture, wherein said mixture is maintained at or above a temperature of about 25° C. for a time and under conditions suitable for increasing the proportion of Form B in said composition.

31. The process of claim 30 wherein said mixture is maintained at a temperature of about 25 to about 60° C.

32. The process of claim 30 wherein form B forms less than 10% by weight of total bazedoxifene acetate in said composition.

33. The process of claim 30 wherein said solvent further comprises ethyl acetate.

34. The process of claim 30 wherein said mixture is heated at reflux temperature for a time period of from about 1 to about 3 hours, cooled to a temperature of from about 40 to about 60° C. over the course of about 1 hour, cooled to about 15 to about 25° C. over the course of about 3 hours, and maintained at a temperature of about 15 to about 25° C. for a time period of from about 8 to about 18 hours.

35. A method of lowering cholesterol in a mammal comprising administering to said mammal a therapeutically effective amount of the polymorph of claim 1.

36. A method of inhibiting bone loss in a mammal comprising administering to said mammal a therapeutically effective amount of the polymorph of claim 1.

37. A method of treating breast cancer in a mammal comprising administering to said mammal a therapeutically effective amount of the polymorph of claim 1.

38. A method of treating a postmenopausal woman for one or more vasomotor disturbances comprising administering to said postmenopausal woman a therapeutically effective amount of the polymorph of claim 1.

39. The method of claim 38 wherein the vasomotor disturbance is hot flush.

40. The crystalline polymorph form B of bazedoxifene acetate prepared by the method of claim 24.

41. The polymorph of claim 1 prepared by the method comprising combining bazedoxifene acetate with a solvent comprising ethanol to form a mixture, wherein said mixture is maintained at or above a temperature of about 25° C. for a time and under conditions suitable for forming said polymorph.

* * * * *